United States Patent [19]

Landowne

[11] 4,157,299

[45] Jun. 5, 1979

[54] TWO-PHASE FILTER AND THIN LAYER CHROMATOGRAPHY PROCESS

[75] Inventor: Robert A. Landowne, Westport, Conn.

[73] Assignee: The United States of America as represented by the Secretary of the Army, Washington, D.C.

[21] Appl. No.: 651,670

[22] Filed: Jan. 22, 1976

[51] Int. Cl.² ............................................. B01D 15/08
[52] U.S. Cl. .................................. 210/31 C; 23/230 R
[58] Field of Search ............ 23/230 R, 230 B, 253 TP; 55/67, 197, 386, 522, 324, 387, 389, 97, 98; 210/31 C, 198 C, 502–504

[56] References Cited

U.S. PATENT DOCUMENTS

| | | | |
|---|---|---|---|
| 875,355 | 12/1907 | Knight | 210/502 |
| 2,890,797 | 6/1959 | Matthews | 23/253 TP |
| 3,510,263 | 5/1970 | Hach | 23/230 R |
| 3,552,295 | 1/1971 | Fetter | 23/253 TP |
| 3,600,306 | 8/1971 | Tocci | 210/31 C |
| 3,647,684 | 3/1972 | Malcomb | 210/31 C |
| 3,893,808 | 7/1975 | Campbell | 23/253 TP |

*Primary Examiner*—John Adee
*Attorney, Agent, or Firm*—Nathan Edelberg; Robert W. Church; Kenneth P. Van Wyck

[57] ABSTRACT

A process of using a two-phase gas or liquid filter and thin layer chromatography member having a filter portion and a chromatography portion. The sample is collected and analyzed on the same member. A developing solvent of substantially acrylonitrile-benzene-petroleum ether is used to allow the sample to chromatograph on the chromatography portion of the member.

4 Claims, No Drawings

TWO-PHASE FILTER AND THIN LAYER CHROMATOGRAPHY PROCESS

BACKGROUND OF THE INVENTION

Thin layer chromatography has become increasingly important in the detection and analysis of filterable materials in liquids and gases in recent years. Both from a military standpoint and in industry, the analysis of liquids and gases has become a major concern. On the one hand, the analysis of liquids and gases on and off the battlefield during warfare is necessary to prevent the unnecessary loss of life while, on the other hand, ecologically, the analysis of gases and liquids for purposes of preventing the pollution of natural resources and injury to humans, animals and vegetation cannot be of more importance.

Thin layer chromatography consists of dividing substances into zones on a thin layer of adsorbent utilizing minute amounts of the substance. The substance is placed on the end of a strip of material which usually contains an adsorbent and that end of the strip is placed in a solvent which has been preselected by virtue of its ability to separate out various components of a particular substance. The substance is separated and emerges as a spot on the adsorbent which can be detected using a number of different known techniques.

Common practice for the analysis of liquid or gaseous samples has been to filter the sample in order to collect the filterable components thereof. Although some samples can be analyzed directly on the filter, many samples are too complex to analyze directly or a particular interference in the analysis of a component of interest may be present on the filter thereby also preventing direct analysis. In such instances, the sample must be removed from the filter and then redeposited for the required thin layer chromatography. As a result, samples are often lost, mishandled or contaminated thereby making analysis difficult and oftimes necessitating the taking of a second sample. Marginal success until the present process invention is evidenced by the Silvestri Patent, U.S. Pat. No. 4,033,720 which involves the use of an overlapped joined filter and absorbent means. It is now assigned to the same assignee as the instant application.

SUMMARY OF THE INVENTION

I have now discovered a novel two-phase gas and liquid filter and thin layer chromatography medium which can be utilized to both collect the sample to be analyzed and subsequently analyze the same. My novel invention avoids the need to remove the sample from the filter and then redeposit it for the required thin layer chromatography step.

The novel filtration and analysis media of the instant invention consists of a support material which is only partially treated with an adsorbent. It may be used to both collect and analyze samples, as mentioned above, whereas commercially available thin layer devices are only suited for analysis because the pores of the support material are completely blocked by the adsorbent and filtration of gases or liquids therethrough is difficult if not impossible.

My novel filter and thin layer chromatography medium is useful in the field of analytical chemistry and air and water pollution as is the method hereinafter disclosed.

DESCRIPTION OF THE INVENTION INCLUDING PREFERRED EMBODIMENTS

As discussed briefly above, I have discovered a novel two-phase gas and liquid filter and thin layer chromatography medium. The medium comprises a support material having from about 75% to about 90% of its total surface area treated with an adsorbent.

The support material may be in the form of a sheet, strip, disc etc. and is treated on all sides such that its surface area is covered with an adsorbent. That is to say, the support material has all its treated surface together and apart from its untreated surface. For example, a sheet, strip or disc of support material can be treated over 75%-90% of its surface area with the adsorbent while the remaining 10-25% of the surface area remains devoid of adsorbent. There cannot be, however, more than one section or area of untreated support surrounded by or adjacent to the treated support area over the surface of the material. That is to say, all the treated area must be one continuous section of the support, all the untreated area must also be continuous and there can only be one non-treated area.

Examples of support material i.e. paper etc., include cellulose, carboxymethyl cellulose, diethylaminoethyl cellulose, ECTEOLA cellulose, cellulose phosphate, cellulose citrate, aminoethyl cellulose; polyethylene terephthalate, fiberglass and the like.

Suitable adsorbents include silica gel; alumina; kieselguhr; diatomaceous earth; powdered cellulose including cellulose phosphate, acetylated cellulose etc.; polyamide powders; ion-exchange powders; calcium sulfate; polyethylene powder; polycaprolactam; hydroxyl-apatite; zinc carbonate; cross-linked dextran; magnesium silicate; calcium hydroxide and the like.

The adsorbent may be added to the support material in any manner known in the art with that described by Bobbitt; Thin-Layer Chromatography; Rheinhold Publishing Corporation; 1963; being preferred, said publication hereby being incorporated herein by reference. Furthermore, the adsorbents may be added in conjunction with binders such as plaster of Paris; starch; polyvinyl alcohol; collodion; decalin; dichlorodimethyl silane and the like in order to ensure good adhesion of the adsorbent to the support.

Phosphors or fluorescent compounds such as zinc silicate luminescent materials; rhodamine 6G; sodium fluorescein; zinc silicate-zinc cadmium sulfide; 2',7'-dichlorofluorescein; morin and the like may be added to the adsorbent, sprayed on the adsorbent or added to the developer solvent mentioned below, for purposes of detecting and visually examining the "spot" formed on the absorbent layer by the filtered material.

In use, my novel medium, the use of which constitutes my novel method, is placed in a suitable apparatus in such a manner that a gaseous or liquid sample may be passed through that portion of the medium which is free of adsorbent. The sample to be analyzed is collected on said untreated portion of my novel medium and is then contacted, preferably in an enclosed system to avoid excessive evaporation of solvent, with a developing solvent. The developing solvent is then allowed to chromatograph up and into the portion of the medium containing the adsorbent material.

A "spot" (chromatogram) then forms on the adsorbent material, which spot may then be visible if colored per se, i.e. is visible to the naked eye or may be made visible by contacting the medium with ultraviolet light in order to detect any fluorescent or luminescent material which may either have been present in the adsorbent when the support was treated therewith or may have been added to the solvent and migrated along the adsorbent therewith. Other known means of detection of the spot such as charring the paper etc. may also be used.

Examples of suitable developer solvents which may be used in my novel process include light petroleum, cyclohexane, carbon tetrachloride, trichloroethylene, toluene, benzene, dichloromethane, chloroform, ethyl ether, ethyl acetate, acetone, n-propanol, ethanol, methanol, carbon disulfide, 1,2-dichloroethane, water, pyriding, heptane, diisobutylene, isopropyl chloride, isopropyl ether, sec. butyl alcohol, pyruvic acid, acetonitrile, organic acids, mixtures of acids or bases, water, alcohols, pyridine etc. and the like. A preferred solvent system I have found exceedingly efficient for the detection of -phenyl-glycolate esters in airborne samples is a 3:1:1 mixture of acetonitrile, benzene and petroleum ether.

The following examples are set forth for purposes of illustration only and are not to be construed as limitations on the instant invention except as set forth in the appended claims. All parts and percentages are by weight unless otherwise specified.

EXAMPLE 1

To a suitable vessel are added 100 parts of an aqueous potassium silicate-ammonium chloride (30/70) solution. Before gelling commences, a strip of glass fiber is dipped into the silicate solution for 15 seconds at a point just below that at which 20% of the strip remains out of the solution. Excess solution is removed and the strip is then air dried for 15 minutes during which time gelling occurs. The resultant strip is then heated to 450° C. to drive off the remaining ammonium chloride.

A sample is collected on the untreated portion of the strip by drawing air through it to filter out the particulate matter to be analyzed. The material trapped in this way is then chromatographed by placing the filter end of the medium into a developing solvent of benzene-acetonitrile-petroleum ether (1:3:1). After separation is accomplished, the spot of interest is detected with ultraviolet light after spraying the adsorbent with a commercially available fluoescent material and quantitated by noting the amount of material found in the spot relative to a standard and to the amount of air passed through the untreated portion during the sampling step. In this example, the detected material is an -phenylglycolate ester.

EXAMPLE 2

The procedure of Example 1 is again followed except that the sample is collected on the filter portion of the treated medium from a previously obtained water sample and the filter is dried before immersing the medium in the solvent mixture. Again the analysis revealed an -phenylglycolate ester.

EXAMPLE 3

The procedure of Example 1 is again followed except the fluorescent material is added to the solvent mixture prior to chromatography of the filtered sample. Similar results are obtained.

EXAMPLE 4

The procedure of Example 1 is again followed except that the fluorescent material is omitted and the portion of the fiberglass strip treated with silicate solution is sprayed after glycolate ester separation is accomplished with a commercially available material which forms a color with said ester. Detection and analysis of the resultant spot is easily accomplished.

EXAMPLES 5-8

Following the procedure of Example 1, various support materials in the form of papers are treated with various adsorbents and used to analyze gaseous and liquid samples. In cases where the adsorbent did not gel onto the support, it was added thereto by dipping the support in a solution or suspension thereof and drying. In each instance, detection and analysis of the separated specimen was accomplished. The results are set forth in Table I, below.

Table 1

| Ex. | Support Material | Adsorbent | Detetion and Analysis Results |
|---|---|---|---|
| 5 | Cellulosic Paper | Alumina | Good |
| 6 | Diethylaminoethyl Cellulose | Ion-exchange Powder | Excellent |
| 7 | Cellulose Citrate | Polyamide Powder | Excellent |
| 8 | Glass Fiber Paper | Cellulose Phosphate | Good |

I claim:

1. A method for detecting filterable materials in gases or liquids which comprises the steps of collecting a gas or liquid sample on the unteated portion of a medium consisting of a support material having from about 75% to about 90% of its surface area continuously treated with an absorbent, contacting the collected sample with a developing solvent of substantial acrylonitrile-benzene-petroleum ether mixture, allowing the sample to chromatograph, and analyzing the resultant developed chromatogram.

2. A method according to claim 1 wherein said support material is fiberglass.

3. A method according to claim 1 wherein said adsorbent is silica gel.

4. A method according to claim 1 wherein said support material is fiberglass and said adsorbent is silica gel.

* * * * *